(12) United States Patent
Siegler et al.

(10) Patent No.: US 7,897,349 B2
(45) Date of Patent: Mar. 1, 2011

(54) MACROPHAGE MIGRATION INHIBITORY FACTOR (MIF) AS MARKER FOR UROLOGICAL INFLAMMATORY DISEASE

(75) Inventors: Katherine Meyer Siegler, Seminole, FL (US); Pedro L. Vera, Largo, FL (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 559 days.

(21) Appl. No.: 11/024,405

(22) Filed: Dec. 30, 2004

(65) Prior Publication Data

US 2005/0176039 A1 Aug. 11, 2005

Related U.S. Application Data

(60) Provisional application No. 60/532,899, filed on Dec. 30, 2003.

(51) Int. Cl.
G01N 33/53 (2006.01)
(52) U.S. Cl. ......................................................... 435/7.1
(58) Field of Classification Search ........................ None
See application file for complete search history.

(56) References Cited

U.S. PATENT DOCUMENTS

| | | | | |
|---|---|---|---|---|
| 5,503,986 | A | * | 4/1996 | Steers et al. ................. 435/7.92 |
| 6,008,003 | A | * | 12/1999 | Haak-Frendscho et al. . 435/7.23 |
| 6,043,044 | A | | 3/2000 | Hudson et al. |
| 2005/0054117 | A1 | | 3/2005 | Giroir et al. |

FOREIGN PATENT DOCUMENTS

WO WO 2004/076679 * 9/2004

OTHER PUBLICATIONS

Vera et al. 'Macrophage migration inhibitory factor is released as a complex with alpha1-inhibitor-3 in the intraluminal fluid during bladder inflammation in the rat.' J. Urology. 174:338-343.*
Joshi et al. 'Trauma patients with positive cultures have higher levels of circulating macrophage migration inhibitory factor (MIF).' Res. Comm. Molec. Path. Pharm. 107(1 & 2):13-20, 2000.*
Meyer Siegler et al. 'Intravesical antibody against macrophage migration inhibitory factor (MIF) reduced substance P induced inflammatory changes in the rat bladder.' Program No. 608.8 2003 Abstract Viewer/Itenerary Planner Washington, DC: Society for Neuroscience, 2003.*
Vera et al. 'Macrophage migration inhibiory factor (MIF) is upregulated in viscero-visceral interactions at the organ and central nervous system levels.' Program No. 608.9. 2003 Abstract Viewer/ Itenerary Planner. Washington, DC:Society for Neuroscience, 2003.*
Meyer-Siegler et al. 'Proinflammatory cytokine upregulation in central and peripheral tissue innercation the bladder in an endotoxin induced model of rat bladder inflammation.' Program No. 71.8. 2002 Abstract Viewer/Itenerary Planner. Washington, DC: Society for Neuroscience, 2002.*
Vera et al. 'Macrophage migration inhibitory factor (MIF) and cyclooxygenase-2 (COX-2) are upregulated in an acid-model of bladder inflammation in rats.' Program No. 71.1. 2002 Abstract Viewer/Itenerary PLanner. Washington, DC: Society for Neuroscience, 2002.*
Pollock et al. 'Laboratory techniques for detection of urinary tract infetion and assessment of value.' Am. J. Med. 75(1B):79-84, 1983.*
Meyer-Siegler et al. 'Macrophage migration inhibitory factor is increased in the urine of patients with urinary tract infection: macrophage migration inhibitory factor-protein complexes in human urine.' J. Urol. 175:1523-1528, 2006.*
Otukesh et al. 'Urine macrophage migration inhibitory factor (MIF) in children with urinary tract infection: a possible predictor of acute pyelonephritis.' Pediatr. Nephrol. Epub Sep. 18, 2008.*
Otukesh et al. 'Urine macrophage migration inhibitory factor in pediatric systemic lupus erythematosus.' Clin. Rheumatol. 26:2105-2107, 2007.*
Matsumoto et al. 'Elevated macrophage migration inhibitory factor (MIF) levels in the urine of patients with focal glomerular sclerosis.' Clin. Exp. Immunol. 139:338-347, 2004.*
Brown et al. 'Urine macrophage migration inhibitory factor reflects the severity of renal injury in human glomerulonephritis.' J. Am. Soc. Nephrol. 13:S7-S13, 2002.*
Brown et al. 'Urine macrophage migration inhibitory factor concentrations as a diagnostic tool in human renal allograft rejection.' 17(12):1777-1783, 2001.*
Matsumoto et al. 'Urinary levels of macrophage migration inhibitory factor in patients with IgA nephropathy.' Nephron 92:309-315, 2002.*
Chai et al. 'Diagnosis of the painful bladder syndrome: current approaches to diagnosis.' Clin. Obst. & Gynec. 45(1):250-258, 2002.*
Erickson et al. 'Urine Markers of Interstitial Cystitis.' Urology 57(Suppl 6A): 15-21, 2001.*
Fernandez et al. 'Anatomical location of macrophage migration inhibitory factor in urogenital tissues, peripheral ganglia and lumbosacral spinal cord of the rat.' Program No. 608.7 Abstract Viewer/Itinerary PLanner. Washington, DC: Society for Neuroscience, 2003.*
Vera et al. 'Anatomical location of macrophage migration inhibitory factor in urogenital tissues, peripheral ganglia and lumbosacral spinal cord of the rat.' BMC Neuroscience 4:17, 2003.*

(Continued)

*Primary Examiner* — Nora M Rooney
(74) *Attorney, Agent, or Firm* — Klarquist Sparkman, LLP

(57) ABSTRACT

The present invention relates to the association between detecting and quantifying the presence of macrophage migration inhibitory factor (MIF) in urine, bladder and prostate tissues for the purpose of diagnosis and prognosis of urological inflammatory. In addition, methods to inactivate MIF activity by use of antibodies or specific MIF inhibitors can be used to treat these diseases. For instance, such diseases as chronic pelvic pain syndrome, non-bacterial prostatitis, and interstitial cystitis may be mediated by MIF release. Periodic assays for MIF could be conducted for a patient to determine if the patient's MIF urine levels are high or increasing. In addition, intravesical MIF antibodies or other MIF-specific inhibitors would reduce or ameliorate these pelvic diseases.

8 Claims, No Drawings

OTHER PUBLICATIONS

Rivas et al. 'Molecular marker for development of interstitial cystitis in rat model: isoactin gene expression.' J. Urology. 157(5):1937-1940, 1997.*

Meyer-Siegler et al. (2005). Substance P induced changes in CD74 and CD44 in the rat bladder. J. Urol. 173(2):615-620.

Vera et al. (2004). Inflamation of the rat prostate evolkes release of macrophage migration inhibitory factor in the bladder: evidence for a viscerovisveral reflex. J. Urol. 172:2440-2445.

Meyer-Siegler et al. (2004). Intraluminal antibodies to macrophage migration Inhibitory factor decrease substance P induced inflamatiory changes in the rat bladder and prostate. J. Urol. 172:1504-1509.

Vera et al. (2003). Hydrocloric acid induced changes in macrophage migration inhibitory factor in the bladder peripheral and central nervous system of the rat. J. Urol. 170:623-627.

Meyer-Siegler et al. (2004). Substance P induced release of macrophage migration inhibitory factor from rat bladder epithelium. J Urol. 171:1698-1703.

Meyer-Siegler et al. (2004). Macrophage migration inhibitory factor is upregulated in an endotoxin-induced model of bladder inflammation in rats. J Interferon & Cytokine Res. 24:55-63.

* cited by examiner

MACROPHAGE MIGRATION INHIBITORY FACTOR (MIF) AS MARKER FOR UROLOGICAL INFLAMMATORY DISEASE

CROSS REFERENCE TO RELATED APPLICATIONS

This claims the benefit of U.S. Provisional Application No. 60/532,899, filed Dec. 30, 2003.

FIELD OF THE INVENTION

The present disclosure relates to the association between detecting and quantifying the presence of macrophage migration inhibitory factor (MIF) in urine, bladder and prostate tissues for the purpose of urological inflammatory disease diagnosis and prognosis. In addition, methods to inactivate MIF activity by use of antibodies or specific MIF inhibitors can be used to treat these diseases. For instance, such diseases as chronic pelvic pain syndrome, non-bacterial prostatitis, and interstitial cystitis may be mediated by MIF release. Periodic assays for MIF could be conducted for a patient to determine if the patient's MIF urine levels are high or increasing. In addition, intravesical MIF antibodies or other MIF-specific inhibitors would reduce or ameliorate these pelvic diseases.

BACKGROUND OF THE INVENTION

MIF is a regulator of inflammation and innate, as well as adaptive, immune responses. However, current research suggests an even greater role for MIF, as it is present in a variety of immune and non-immune cells (Baugh et al., Crit. Care Med. 30: Suppl. S27-S35, 2002). MIF is constitutively expressed in tissues such as the anterior pituitary, prostate epithelia (Meyer-Siegler et al., Diag. Mol. Path. 7:44-50, 1998; and Meyer-Siegler, Cytokine 12:914-921, 2000), gastric, small intestinal and colonic epithelia (Maaser et al., Gastroenterology 122:667-680, 2002), neuronal and non-neuronal cells in the brain (Bacher et al., Mol. Med. 4:217-230, 1998).

As a proinflammatory cytokine, MIF counter-regulates the effects of glucocorticoids (Baugh et al., Crit. Care Med. 30: Suppl. S27-S35, 2002; and Lue et al., Microbes and Infection 4:449-460, 2002). Therefore, MIF has been proposed to play a critical role in immune and inflammatory diseases including septic shock (Bernhagen et al., Nature 365:756-793, 1993), rheumatoid arthritis (Leech et al., Arthritis & Rheumatism 42:1601-1608, 1999), delayed-type hypersensitivity (Brown et al., Transplantation 71:1777-1783, 2001), Crohn's disease (De Jong et al., Nature Immunology 2:1061-1066, 2001), gastric ulcer formation (Vera et al., Brain Res. Bulletin 29:651-658, 1992), and prostate cancer (Meyer-Siegler et al., Diag. Mol. Path. 7:44-50, 1998; and Meyer-Siegler, Cytokine 12:914-921, 2000). Treatment with anti-MIF antibodies has been reported to prevent experimental colitis and treat established colitis in experimental animals (De Jong et al., Nature Immunology 2:1061-1066, 2001). Therefore, anti-MIF therapy might represent a potentially useful therapeutic tool in the treatment of different inflammatory conditions.

As a new and novel finding we have determined that the urothelium is a rich source of pre-formed MIF. MIF is released from the bladder epithelium upon induction of inflammation and inactivation of released MIF by intravesical anti-MIF antibody reduces inflammation in the bladder, prostate and the spinal cord. These results suggest that this knowledge may have commercial application.

MIF was first described thirty years ago and was designated as a cytokine, a chemical mediator, which regulates cell growth by inducing the expression of specific target genes. The initial described function of MIF was as a regulator of inflammation and immunity. It is expressed in the brain, and eye lens, is a delayed early response gene in fibroblasts, and it has been reported that this protein can be found in prostate tissues. MIF has been shown to be a pituitary, as well as macrophage cytokine and a critical mediator of septic shock. Recent studies also suggest that MIF may have an autocrine function for embryo development and is produced by the Leydig cells of the testes. Thus, it appears that this cytokine may play a fundamental role in cell growth regulation and possibly development.

U.S. Pat. No. 6,043,044 discloses the use of prostate tissue extracts as a patient sample to determine the amount of MIF. Immuno- and RNA blot analysis performed using homogenized tissue that contains variable proportions of epithelial and stromal cells still determined significant differences in the levels of MIF protein produced by metastatic tissue (490.3+/−71.3 ng/mg total protein). In practice this test was unreliable and difficult to perform because of contamination with surrounding connective and stromal tissue. It does not have utility in patient diagnosis or prognosis. Further, the patent does not mention or correlate urine, bladder tissue, and/or prostate tissue MIF levels with urological inflammatory disease. Therefore, a need exists for an improved assay with commercial application that is less invasive than that of the prior art.

SUMMARY OF THE INVENTION

The present invention provides methods for detecting or diagnosing or prognosticating urological inflammatory disease. The methods comprise determining the levels of macrophage migration inhibitory factor (MIF) in an individual's urine, bladder tissue, and/or prostate tissue.

The present invention further provides methods for monitoring the treatment of an individual with urological inflammatory disease. The methods comprise administering a pharmaceutical composition to an individual and determining the levels of MIF in the urine, bladder tissue, and/or prostate tissue.

The present invention further provides methods for screening for an agent capable of modulating the onset or progression of urological inflammatory disease. The methods comprise exposing an individual to the agent and determining the levels of MIF in the individual's urine, bladder tissue, and/or prostate tissue.

In embodiments of the present invention, levels of MIF are determined by detecting MIF gene product in the urine, bladder tissue, and/or prostate tissue using immunoassays or nucleic acid analysis, preferably mRNA. Gene products as recited herein can be nucleic acid (DNA or RNA) and/or proteins. In the case of DNA and RNA, detection occurs through hybridization with oligonucleotide probes. In the case of proteins, detection occurs though various protein interaction. Because MIF in urine is measured, the present invention can provide a non-invasive test for urological inflammatory disease.

The urine, bladder tissue, and/or prostate tissue test of the present invention can be used alone or in conjunction with commonly used methods diagnosis.

DESCRIPTION OF THE PREFERRED EMBODIMENT

Many biological functions are accomplished by altering the expression of various genes through transcriptional (e.g., through control of initiation, provision of RNA precursors, RNA processing, etc.) and/or translational control. For example, fundamental biological processes such as cell cycle, cell differentiation and cell death, are often characterized by the variations in the expression levels of individual gene or group of genes.

Changes in gene expression also are associated with pathogenesis. For example, the lack of sufficient expression of functional tumor suppressor genes and/or the over expression of oncogene/protooncogenes could lead to tumorgenesis or hyperplastic growth of cells (Marshall, *Cell* 64:313-326, 1991; Weirlberg, *Science* 254:1138-1146, 1991). Thus, changes in the expression levels of particular gene or group of genes (e.g., oncogenes or tumor suppressors) serve as signposts for the presence and progression of various diseases.

Monitoring changes in gene expression may also provide certain advantages during drug screening development. Often drugs are screened and prescreened for the ability to interact with a major target without regard to other effects the drugs have on cells. Often such other effects cause toxicity in the whole animal, which prevent the development and use of the potential drug.

The present inventors have identified MIF, in urine, bladder tissue, and/or prostate tissue, as a gene marker associated with urological inflammatory disease. Changes in MIF can also provide useful markers for diagnostic uses as well as markers that can be used to monitor disease states, disease progression, drug toxicity, drug efficacy and drug metabolism.

Use of MIF as Diagnostics

As described herein, the MIF in urine, bladder tissue, and/or prostate tissue may be used as diagnostic markers for the prediction or identification of urological inflammatory disease. For instance, a urine, bladder tissue, and/or prostate tissue sample from a patient may be assayed by any of the methods described herein or by any other method known to those skilled in the art, and the expression levels of MIF may be compared to the expression levels found in normal urine, bladder tissue, and/or prostate tissue. The expression levels of MIF in urine, bladder tissue, and/or prostate tissue that substantially resemble an expression level from the urine, bladder tissue, and/or prostate tissue of normal or of diseased patients may be used, for instance, to aid in disease diagnosis and/or prognosis. Comparison of the MIF levels may be done by researcher or diagnostician or may be done with the aid of a computer and databases.

Use of MIF for Drug Screening

According to the present invention, MIF levels in urine, bladder tissue, and/or prostate tissue may be used as markers to evaluate the effects of a candidate drug or agent on urological inflammatory disease patients.

A patient is treated with a drug candidate and the progression of the disease is monitored over time. This method comprises treating the patient with an agent, obtaining a urine, bladder tissue, and/or prostate tissue sample from the patient, determining levels of MIF in the urine, bladder tissue, and/or prostate tissue, and comparing the levels of MIF over time to determine the effect of the agent on the progression of the disease.

The candidate drugs or agents of the present invention can be, but are not limited to, peptides, small molecules, vitamin derivatives, as well as carbohydrates. Dominant negative proteins, DNA encoding these proteins, antibodies to these proteins, peptide fragments of these proteins or mimics of these proteins may be introduced into the patient to affect function. "Mimic" as used herein refers to the modification of a region or several regions of a peptide molecule to provide a structure chemically different from the parent peptide but topographically and functionally similar to the parent peptide (see Grant (1995), in *Molecular Biology and Biotechnology*, Meyers (editor) VCH Publishers). A skilled artisan can readily recognize that there is no limit as to the structural nature of the candidate drugs or agents of the present invention.

Use of MIF for Monitoring Disease Progression

As described above, the expression of MIF in urine, bladder tissue, and/or prostate tissue may also be used as markers for the monitoring of disease progression, for instance, the development of urological inflammatory disease. For instance, a urine, bladder tissue, and/or prostate tissue sample from a patient may be assayed by any of the methods described above, and the expression levels in the sample of MIF may be compared to the expression levels found in normal urine, bladder tissue, and/or prostate tissue. The MIF in urine, bladder tissue, and/or prostate tissue can be monitored over time to track progression of the disease. Comparison of the MIF levels may be done by researcher or diagnostician or may be done with the aid of a computer and databases.

Assay Formats

The over expression of MIF is manifest at both the level of messenger ribonucleic acid (mRNA) and protein. It has been found that increased MIF in urine, bladder tissue, and/or prostate tissue, determined by either mRNA levels or biochemical measurement of protein levels using immunoassays, is associated with urological inflammatory disease.

In an embodiment of the present invention, urine, bladder tissue, and/or prostate tissue MIF levels are detected by immunoassays. Generally, immunoassays involve the binding of the MIF and anti-MIF antibody. The presence and amount of binding indicate the presence and amount of MIF present in the sample. Examples of immunoassays include, but are not limited to, ELISAs, radioimmunoassays, and immunoblots, which are well known in the art. The antibody can be polyclonal or monoclonal and is preferably labeled for easy detection. The labels can be, but are not limited to biotin, fluorescent molecules, radioactive molecules, chromogenic substrates, chemi-luminescence, and enzymes.

In a preferred embodiment, ELISA, based on the capture of MIF by immobilized monoclonal anti-MIF antibody followed by detection with biotinylated polyclonal anti-MIF antibody, is used to detect MIF. In this system, the wells of a multi-well plate are coated with the monoclonal antibody and blocked with milk (albumin blocking should be avoided because MIF has been shown to bind albumin). Urine, bladder tissue, and/or prostate tissue samples are then added to the wells and incubated for capture of MIF by the monoclonal antibody. The plate is then detected with the polyclonal antibody and strepavidine-alkaline phosphatase conjugate.

In another embodiment, urine, bladder tissue, and/or prostate tissue MIF levels are detected by measuring nucleic acid levels in the urine, bladder tissue, and/or prostate tissue, preferably MIF mRNA. This is accomplished by hybridizing the nucleic acid in the urine, bladder tissue, and/or prostate tissue with oligonucleotide probes that is specific for the MIF gene.

Nucleic acid samples used in the methods and assays of the present invention may be prepared by any available method or process. Methods of isolating total RNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I—Theory and Nucleic Acid Preparation, Tijssen, (1993) (editor) Elsevier Press. Such samples include RNA samples, but also include cDNA synthesized from a mRNA sample isolated from a cell or tissue of interest. Such samples also include DNA amplified from the cDNA, and an RNA transcribed from the amplified DNA. One of skill in the art would appreciate that it is desirable to inhibit or destroy RNase present in homogenates before homogenates can be used.

Nucleic acid hybridization simply involves contacting a probe and target nucleic acid under conditions where the probe and its complementary target can form stable hybrid duplexes through complementary base pairing (see U.S. Pat. No. 6,333,155 to Lockhart et al, which is incorporated herein by reference). Methods of nucleic acid hybridization are well known in the art. In a preferred embodiment, the probes are immobilized on solid supports such as beads, microarrays, or gene chips.

The hybridized nucleic acids are typically detected by detecting one or more labels attached to the sample nucleic acids and or the probes. The labels may be incorporated by any of a number of means well known to those of skill in the art (see U.S. Pat. No. 6,333,155 to Lockhart et al, which is incorporated herein by reference). Commonly employed labels include, but are not limited to, biotin, fluorescent molecules, radioactive molecules, chromogenic substrates, chemiluminescent labels, enzymes, and the like. The methods for biotinylating nucleic acids are well known in the art, as are methods for introducing fluorescent molecules and radioactive molecules into oligonucleotides and nucleotides.

Detection methods, for both the immunoassays and the nucleic acid assays, are well known for fluorescent, radioactive, chemiluminescent, chromogenic labels, as well as other commonly used labels. Briefly, fluorescent labels can be identified and quantified most directly by their absorption and fluorescence emission wavelengths and intensity. A microscope/camera setup using a light source of the appropriate wavelength is a convenient means for detecting fluorescent label. Radioactive labels may be visualized by standard autoradiography, phosphor image analysis or CCD detector. Other detection systems are available and known in the art.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

EXAMPLE 1

Changes in MIF and cox-2 Due to Acid-Induced Bladder Inflammation in Rats

The presence of MIF in the lower urinary tract of the rat had not been examined previously. We evaluated the presence of MIF in the bladder, the major pelvic ganglia (MPG), the L6/S1 dorsal root ganglia (DRG) and the L6/S1 spinal cord of control rats. The MPG provides parasympathetic innervation to the bladder, whereas the L6/S1 DRG contains the afferent neurons innervating the bladder via the pelvic nerves (Vera et al., *Brain Res. Bulletin* 29:651-658, 1992). The L6/S1 spinal cord integrates afferent input from the bladder and other pelvic organs (Vera et al., *Brain Research* 883:107-118, 2000; Nadelhaft et al., *BMC Neurosci.* 3:8, 2002; Nadelhaft et al., *J. Comparative Neurology* 375:502-517, 1996; and Nadelhaft et al., *J. Comparative Neurology* 359:443-456, 1995) and relays the information to brain areas that are responsible for micturition. The L6/S1 then sends efferent output to the MPG, resulting in a bladder contraction. The materials and methods are identical to those disclosed in Vera et al. (*Journal of Urology* 170:623-627, 2003), the disclosure of which is incorporated herein by reference.

In saline-treated bladder, the epithelia showed considerable MIF immunostaining restricted to basal and intermediate layers, and not on the superficial cells. MIF protein was detected by Western blotting in all of the tissues examined. MIF mRNA was also detected in all the tissues examined. Therefore, MIF is constitutively expressed in the bladder, the lumbosacral spinal cord, the L6/S1 DRG and the MPG of the rat. Bladder inflammation induced by acid instillation into the bladder resulted in a marked increase in the MIF content and mRNA in the spinal cord, the DRG and the MPG. These results established that MIF is constitutively expressed in the bladder and the central and peripheral sites innervating it. Most of the MIF in the bladder was located in the bladder epithelia. These are novel findings. Moreover, bladder inflammation produced by an acid insult to the bladder resulted in upregulation of MIF and cox-2 protein in central and peripheral nervous structures, suggesting that MIF may play a role in bladder inflammation, at the organ level and at central and peripheral sites. These results are discussed in further detail in Vera et al. (*Journal of Urology* 170:623-627, 2003), which has been incorporated herein by reference.

EXAMPLE 2

Up-Regulation of MIF and Cox-2 in a Bacterial Endotoxin Model of Bladder Inflammation in the Rat Intravesical instillation of a bacterial endotoxin (lipopolysaccharide from *E. Coli*) has been documented to produce histological signs of bladder inflammation (Stein et al., *J. Urol.* 155: 1133-1138, 1996; Saban et al., *Am. J Pathol.* 160: 2095-2110, 2002; Wheeler et al., *Eur. J Pharmacol.* 417: 239-248, 2001). In addition, LPS has been shown to induce a pro-inflammatory cascade that may involve MIF (Roger et al., *Nature* 416:920-924, 2001). Therefore, we examined the effects of intravesical LPS on the levels of MIF and cox-2 on the bladder, lumbosacral spinal cord, DRG and MPG. In LPS treated rats, significant increases in MIF protein and mRNA were observed in all the tissues, including the bladder. Therefore, intravesical LPS resulted in marked histological changes indicative of cystitis that are in agreement with previous reports (Stein et al., *J. Urol.* 155:1133-1138, 1996). These are also novel findings and suggest that MIF may be involved in bladder inflammation caused by bacterial infection. The fact that similar changes in MIF and cox-2 were observed in the spinal cord and DRG suggests that MIF may be involved in neurogenic inflammation, regardless of how it is initially started. Data from LPS treated rats suggest that MIF may be involved in the first steps of the immune/inflammatory response against infections. Materials and methods, and the results are discussed in further details in Meyer-Siegler et al. (Journal of Interferon and Cytokine Research 24(1):55-63, 2004), the disclosure of which is incorporated herein by reference.

EXAMPLE 3

Substance P-Induced Changes in MIF in the Bladder and the Prostate

Release of tachykinins (such as substance P) from small, capsaicin-sensitive afferent terminals at the target organ causes plasma extravasation, edema and swelling. Substance P (SP) plays a major role in the development of neurogenic inflammation in the bladder produced by electrical stimulation of the nerves that innervate the bladder thus producing release of neurotransmitter from the afferent terminals (Koltzenburg et al., *Neurosci. Lett.* 72: 352-356, 1986). Alternatively, plasma extravasation and edema can be elicited in the bladder from systemic injections of SP (Saria et al. *Naunyn-Schmiedeberg's Arch. Pharmacol.* 324:212-218, 1983; Abelli et al., *J. Auton. Pharmacol.* 12:269-276, 1992; Abelli et al., *J. Auton. Pharmacol.* 9: 253-263, 1989; and Gao et al., *Reg. Peptides,* 58:117-121, 1995).

We sought to determine if neurogenic inflammation alone (without producing damage or insult to the bladder epithelia, as was the case in the acid and LPS cystitis models) was also able to alter MIF levels in the bladder. In addition, we examined the prostate for signs of inflammation. Systemic injections of SP elicited plasma extravasation and edema (neurogenic inflammation) in the bladder and the prostate. We examined MIF and cox-2 to compare the results with our previous models of bladder injury (acid and LPS). In addition, we examined nerve growth factor (NGF) and the proto-oncogene c-fos.

NGF is widely regarded as a critical mediator of inflammatory pain and hyperalgesia (McMahon et al., *Nature Med.* 1: 774-780, 1995; and Woolf et al., *Neuroscience* 62:327-331, 1994). The effects of NGF are complex, involving peripheral as well as central nervous system sites. Inflammation results in an increase in NGF levels that may act to sensitize small-diameter afferent fibers (Dmitrieva et al., *Pain* 66:87-97, 1996; and Shu et al., *J. Neurophysiol.* 86:2931-2938, 2001). In addition, intravesical NGF itself produces bladder hyperreflexia suggestive of inflammatory pain (Chuang et al., *J. Urol.* 165:975-979, 2001) probably by exciting and sensitizing small diameter afferent fibers, including $A\delta$ and C-fibers (Dmitrieva et al., *Pain* 66:87-97, 1996). NGF is also increased in the bladder of patients with interstitial cystitis (Lowe et al., *Br. J. Urol.,* 79:572-577, 1997) and in the seminal plasma of patients with chronic pelvic pain syndrome (CPPS) (Miller et al., *Urol.* 59:603-608, 2002), suggesting that it may play a role in both of these conditions.

We also examined c-fos changes in the bladder. c-fos is an early proto-oncogene involved in signal transduction cascades. Recently, Saban et al. (*Am. J. Pathol.,* 160:2095-2110, 2002) showed that c-fos is upregulated in the bladder of the mouse after LPS or SP. In addition, c-fos in widely used as a neuronal maker for activation from noxious stimulation. c-fos increased in the spinal cord because of bladder or prostate inflammation (Ishigooka et al., *J. Urol.* 164:1751-1756, 2000). NGF, acting at trkA receptors activates Ras and ERK signaling pathways to result in transcription of c-fos (Friedman et al., *Exp. Cell Research* 253:131-142, 1999). c-fos and c-jun bind to the AP-1 site to regulating several other gene products, including MIF (Onodera et al., *J. Biol. Chem.* 277: 7865-74, 2002).

SP treatment resulted in severe edema in the lamina propria of the bladder (Mean=2.69±0.1; $p<0.05$) when compared to the saline treated rats (Mean=0.23±0.6). The bladders and prostates of animals that had been treated with SP showed a marked decrease in the content of MIF when compared to those treated with saline. MIF levels in the urine and serum of SP treated animals with isolated bladders were significantly increased. Therefore, in this model of neurogenic inflammation (plasma extravasation caused by SP), MIF is released into the urine from the bladder. NGF levels were significantly elevated in the prostate and the urine, but not in the bladder of SP treated rats. Finally, cox-2 and c-fos levels in the bladder and the prostate were significantly elevated in the SP group.

In summary, systemic SP, a model of neurogenic inflammation in the bladder and other organs, resulted in histological changes suggestive of inflammation. In addition, MIF protein content decreased in the bladder while it increased in the urine, suggesting that MIF was released into the urine as a result of SP. Other inflammatory markers, such as cox-2, c-fos and NGF also increased in the bladder as a result of SP treatment. Materials and methods, and the results are discussed in further details in Meyer-Siegler et al. (*Journal of Urology* 171(4):1698-1703, 2004), the disclosure of which is incorporated herein by reference.

EXAMPLE 4

Formalin Injection in the Prostate Causes Urodynamic, Molecular and Histological Changes in the Bladder Consistent with Bladder Inflammation: A Model of Non-Bacterial Prostatitis Chemical irritation of the prostate results in increased substance P in the L6/S1 spinal cord (Ishigooka et al., *Urology,* 59:139-144, 2002). In addition, irritation of the prostate or the bladder results in similar patterns of plasma extravasation and distribution of c-fos stained neurons in the L6/S1 spinal cord (Ishigooka et al., *J. Urol.,* 164:1751-1756, 2000). Recent anatomical evidence showed the prostate and the bladder receive afferent and efferent innervation from largely separate groups of neurons located in similar and overlapping areas of the central and peripheral nervous system (Nadelhaft et al., *BMC Neurosci.* 3:8, 2002). Therefore, it is possible that activation of one organ may affect the functioning of the other organ through central overlap of projection areas.

In CPPS, prostatic inflammation is suspected to result in referred visceral pain and urodynamic changes. Therefore, we established a model of prostatitis that would allow the study of histological, molecular and physiological changes in the bladder and the prostate, in an effort to correlate it to visceral referred pain. We sought to determine if chemical irritation of the prostate resulted in physiological and molecular changes in the bladder indicative of bladder inflammation. In addition, since our preliminary evidence showed that MIF levels changed in a neurogenic model of inflammation and neurogenic inflammation has been implicated in both CPPS and IC, we aimed to investigate if MIF played a role in this process.

Formalin injection into the prostate resulted in inflammation of the prostate, compared to control animals. Similarly, there was significant submucosal edema and increased submucosal vasodilatation in the bladders of animals that were injected with formalin in the prostate, compared to saline injections.

Injection of formalin into the prostate resulted in an almost immediate significant decrease in the bladder intercontraction interval. This bladder hyperreflexia was maximal in the first ten minutes after injection; however, it persisted for the entire observation period (60 min). The MIF protein level in the bladder was significantly reduced in the animals receiving formalin in the prostate. Interestingly, changes were also observed in the levels of MIF in the central nervous system with the protein levels increasing in the lumbosacral cord while decreasing in the cervical cord. MIF and cox-2 mRNA levels also increased in the bladder and in the L6-S1 cord due to prostate inflammation.

Therefore, in this experiment we showed that chemical irritation of the prostate results in bladder hyperreflexia that persists for at least 1 hour. The observed molecular and histological changes were also consistent with bladder inflammation. In addition, MIF and cox-2 levels in the spinal cord also increased after prostate inflammation suggesting that spinal activation results in MIF protein increase and activation of prostanoid synthesis. Finally, MIF levels in the bladder decreased indicating MIF release into the urine, consistent with our previous findings of neurogenic inflammation in the bladder. Materials and methods, and the results are discussed in further details in Meyer-Vera et al. (*Journal of Urology* 172(4):2440-2445, 2004), the disclosure of which is incorporated herein by reference.

EXAMPLE 5

Human Bladder Epithelial Cells Synthesize and Secrete MIF in vitro

In order to establish the relevance of MIF to urogenital disease in humans we sought to determine if MIF was present in human bladder epithelial cells. Human bladder HT-1376 cells (ATCC, Manasas, Va.) were cultured for 48 hours and the culture medium was assayed for MIF using ELISA. In addition, intracellular content of MIF was assayed from cell lysates. These human bladder epithelial cells synthesize MIF (226±0.6 μg/mg protein). The average MIF concentration secreted into the medium by these cells was 15 ng/ml. Expression of MIF was confirmed by RT-PCR analysis. Thus establishing the presence of MIF in human bladder epithelia.

EXAMPLE 6

Intravesical MIF Prevents or Reverses Neurogenic Inflammation in the Bladder and the Prostate MIF is released by bladder epithelia into the bladder lumen, therefore it is possible that MIF release is participating in an autocrine loop that amplifies or maintains inflammatory processes within the bladder. We determined whether it was possible to disrupt the inflammatory loop by neutralizing MIF intravesically. Our hypothesis is that MIF may be involved in the initiation or the continuation of inflammatory processes; therefore, blockade of intravesical MIF with anti-MIF antibodies may be able to prevent or reverse neurogenic inflammation.

Systemic administration of SP was used as a model of neurogenic inflammation. Based upon previous data a 60 min waiting time post-SP, which resulted in the largest increase of urinary MIF was chosen. Intravesical anti-MIF prevented inflammatory changes due to SP. SP decreased MIF protein in the bladder of animals receiving intravesical saline. Bladder MIF was released into the urine. SP increased nerve growth factor, cox-2 and c-fos levels in both the bladder and prostate of animals treated with either intravesical saline or non-specific antibody. However, pre-treatment with intravesical anti-MIF prevented or reduced all of these changes. Histological examination showed that intravesical MIF decreased edema in the bladders of SP treated animals. Intravesical treatment with anti-MIF also prevented SP induced inflammatory changes in the prostate. These data suggest that reducing inflammation in one pelvic organ may also decrease inflammation in a nearby pelvic organ. These data also suggest that MIF released into the urine may be sustaining or amplifying the neurogenic inflammation. These data support the hypothesis that MIF is a mediator of visceral referred pain and is a logical novel therapeutic target in pelvic pain conditions. In addition, detection of elevated MIF in the urine is an indication of pelvic inflammatory disease processes.

EXAMPLE 7

Substance P Induced Changes in CD 74 and CD 44 in the Rat Bladder

Substance P (SP) induces rat bladder inflammation aling with release of the proinflammartory citokine, MIF. To describe the mechanism of MIF action, we examined changes in the amount of CD74 (membrane receptor for MIF), CD44, and phospho-(p-ERK)1/2 in the bladder.

The materials and methods are identical to Meyer-Siegler et al. (*Journal of Urology* 173: February, 2005), the disclosure of which is incorporated herein by reference. In anesthetized rats, the bladder was isolated by cutting the ureters and urine was replaced by saline as intraluminal fluid (ULF). One hour after subcutaneous SP (40 μg/kg) or saline administration, the ILF and bladder were collected. Bladder tissue was analyzed for CD74 and CD44 by immunohistochemistry. Western blot analysis determined the relative amounts of bladder tissue MIF, CD74, CD44, and p-ERK1/2. ILF immunoprecipitation followed by Western blot analysis was performed to identify an association of MIF with CD74 and/or CD44

SP induced significant MIF release from the bladder and increased CD74 and CD44 bladder immunostaining. SP treatment increased the total amount of bladder CD74 protein and mRNA, intracellular domain CD44, p-ERK1/2 and soluble CD44 in the ILF. Finally, MIF was found to be associated with soluble CD44 in the ILF.

CD74 was present in the rat urothelium. SP increased CD74 and intracellular domain CD44 in the baldder, while stimulated the release of soluble CD44 and MIF into the ILF. MIF interacted with soluble CD44 in the ILF and was available to bind with CD74 in the bladder to exert proinflammatory effects. These results are discussed in further detail in Meyer-Siegler et al. (*Journal of Urology* 173: February, 2005), which has been incorporated herein by reference.

EXAMPLE 8

Intraluminal Antibodies to MIF Decrease Substance P Induced Inflammatory Changes in the Bladder and Prostate Noxious stimuli induce substance P (SP) secretion from nerve terminals, resulting in plasma extravasation, edema and hyperalgesia, commonly referred to as neurogenic inflammation. Because SP is a short-lived molecule, additional proinflammatory mediators maintain continued inflammation. The bladder contains stores of preformed MIF, a proinflammatory cytokine, which is released into the lumen in response to SP. MIF may act in an amplifying manner to maintain or increase inflammation. Inducing inflammatory changes with SP, while sequestering released luminal MIF with an antibody, tested this hypothesis.

The materials and methods are identical to Meyer-Siegler et al. (*Journal of Urology* 172:1507-1509,2005), the disclosure of which is incorporated herein by reference. In anesthetized rats the ureters were cut to isolate the bladder and the bladder contents were replaced with saline or antiMIF antibody (5 or 15 μg/ml), immediately followed by systemic SP or saline. Changes in the expression of inflammatory cytokines, andhistological changes in the bladder and prostate were evaluated 1 hour later.

Targeted array analysis identified increases in proinflammatory gene expression in the bladder and prostate as a result of SP. SP induced changes in MIF, cyclooxygenase-2, nerve growth factor, c-fos and edema were decreased by intraluminal anti-MIF.

SP increased MIF amounts in the bladder lumen. Sequestering luminal MIF with an antiMIF antibody decreased SP induced inflammatory changes in the bladder and prostate, suggesting that MIF is involved in acute pelvic visceral neurogenic inflammation. These data indicate that MIF released from the bladder sustains or amplifies SP induced inflammation, a possibility that agrees with known MIF proinflammatory functions. These data continue to support our hypothesis that MIF is a new target for intervention in pelvic viscera inflammation. These results are discussed in further detail in Meyer-Siegler et al. (*Journal of Urology* 172:1507-1509, 2005), which has been incorporated herein by reference.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for detecting or diagnosing interstitial cystitis in an individual comprising:
   determining levels of macrophage migration inhibitory factor (MIF) in a urine sample from the individual and in a bladder sample from the individual by immunoassay;
   comparing the level of MIF in the urine sample from the individual with a level of MIF in a control urine sample and comparing the level of MIF in the bladder sample from the individual with a level of MIF in a control bladder sample; and
   detecting or diagnosing interstitial cystitis in the individual if an increase of MIF level in the urine sample from the individual and a decrease of MIF level in the bladder sample from the individual as compared to the control samples is detected.

2. The method of claim 1, wherein the immunoassay is ELISA.

3. The method of claim 1, wherein the immunoassay is an immunoblot.

4. The method of claim 1, wherein the determining step comprises:
   contacting the urine sample from the individual with an antibody that specifically binds the macrophage MIF;
   contacting the bladder sample from the individual with an antibody that specifically binds the macrophage MIF; and
   detecting the presence of binding between the macrophage MIF and the antibody in the urine sample and the bladder sample.

5. The method of claim 4, wherein the antibody is selected from the group consisting of monoclonal antibodies and polyclonal antibodies.

6. The method of claim 4, wherein the antibody is labeled.

7. The method of claim 6, wherein the label is selected from the group consisting of biotin, fluorescent molecules, radioactive molecules, chromogenic substrates, chemiluminescent labels, and enzymes.

8. The method of claim 1, further comprising the step of comparing the levels of MIF in the urine of the individual to the MIF levels of patients having bladder inflammation.

* * * * *